US007199378B2

(12) United States Patent
Ishiura et al.

(10) Patent No.: US 7,199,378 B2
(45) Date of Patent: Apr. 3, 2007

(54) METHOD FOR MEASURING AND ANALYZING BIOLUMINESCENCE AND DEVICE FOR MEASURING AND ANALYZING BIOLUMINESCENCE

(75) Inventors: Masahiro Ishiura, Nagoya (JP); Kazuhisa Okamoto, Nagoya (JP)

(73) Assignee: Nagoya University, Nagoya (JP)

( * ) Notice: Subject to any disclaimer, the term of this patent is extended or adjusted under 35 U.S.C. 154(b) by 215 days.

(21) Appl. No.: 10/791,713

(22) Filed: Mar. 4, 2004

(65) Prior Publication Data

US 2004/0232351 A1    Nov. 25, 2004

(30) Foreign Application Priority Data

Mar. 7, 2003   (JP)   ............... 2003-061203

(51) Int. Cl.
*A61B 6/00*   (2006.01)
(52) U.S. Cl. ................................. 250/461.2
(58) Field of Classification Search ............ 250/461.2, 250/461.1
See application file for complete search history.

(56) References Cited

U.S. PATENT DOCUMENTS 6,806,954 B2 *  10/2004  Sandstrom ................. 356/317

6,977,722 B2 *  12/2005  Wohlstadter et al. ....... 356/246

FOREIGN PATENT DOCUMENTS

JP   A 2000-346799   12/2000
JP   A 2002-312781   10/2002

OTHER PUBLICATIONS

Gregg C. Allen et al.; "Real-time analysis of rhythmic gene expression in immortalized suprachiasmatic nucleus cells"; Neuroreport, vol. 13, No. 16, Nov. 15, 2002.
Kamiya, K., "Image Processing in Biotechnology Field," (*ARGUS Series*), vol. 0QD-92, Nos. 61-62, 64-65, 1992, pp. 9-15 and English translation.
Takao Kondo et al., "Molecular Mechanism of the Biological Clock of Cyanobacteria: Monitoring the Biological Clocks by Bioluminescence", pp. 62-65, 1997.

* cited by examiner

*Primary Examiner*—Otilia Gabor
(74) *Attorney, Agent, or Firm*—Oliff & Berridge, PLC

(57) ABSTRACT

A method for measuring and analyzing bioluminescence, including the steps of receiving in real-time a luminescence measurement result group from a creature sample group, displaying and maintaining in real-time the luminescence measurement result group, receiving in real-time another luminescence measurement result group from the creature sample group, and displaying and maintaining in real-time the another luminescence measurement result group, instead of the luminescence measurement result group.

12 Claims, 7 Drawing Sheets

METHOD FOR MEASURING AND ANALYZING BIOLUMINESCENCE AND DEVICE FOR MEASURING AND ANALYZING BIOLUMINESCENCE

BACKGROUND OF THE INVENTION

1. Field of the Invention

This invention relates to a method for measuring and analyzing bioluminescence and an apparatus for measuring and analyzing bioluminescence. This invention also contains a program for real-time monitoring and analyzing of bioluminescence data such as circadian bioluminescence rhythms. This invention is preferably useful in genetic screening of mutants for the research of gene expression, especially, research for the biological rhythms using bioluminescence reporter genes. Herein, the rhythm measurement and analysis is originated from that the biometry repeats one day periodic cycle with time within several days of measurement and analysis.

2. Description of the Prior Art

In a conventional measurement of bioluminescence, a tabular software program and an analysis software program for data processing can not be driven with a control software program of a bioluminescence measurement device simultaneously because the CPU is overloaded and OS (operation system) in the computer become to be unstable. In this point of view, measurement results are stored as text file in a memory of the bioluminescence measurement apparatus through the control on the control software program, transferred into the tabular software program, and analyzed in data by utilizing an external software program (see, Non-Patent document 1).

[Non-patent document 1]

"Novel features of Drosophila period transcription revealed by real-time luciferase reporting" by Christian Brandes et al., Neuron, Vol. 16, pp687–692

Therefore, the measurement results can not be recognized in real-time by an operator, so that the measurement condition and the like can not be controlled flexibly on the measurement results. Moreover, since the conventional bioluminescence measurement apparatus does not contain any statistical processing functions, we can not analyze large-scaled measurement results rapidly and it requires much time in the judgment of the results (in this case, the measurement is stopped). Particularly, it requires much time in the selection of mutants in a large-scaled genetic screening of mutant using bioluminescence. Therefore, the bioluminescence measurement apparatus can not be utilized effectively.

Bioluminescence real-time measurement is effective in the comprehensive screening of mutants relating to the key gene expression because we can monitor gone expression continuously as bioluminescence from living cells, so expected as effective measurement in comprehensive analysis of genome function. With conventional bioluminescence measurement apparatus, however, a large-scaled measurement and analysis can not be realized.

SUMMARY OF THE INVENTION

It is an object of the present invention to provide a method and an apparatus for measuring and analyzing bioluminescence which are based on the conventional bioluminescence real-time measurement.

In order to achieve the above object, this invention relates to a method for measuring and analyzing bioluminescence, comprising the steps of:

receiving in real-time a luminescence measurement result group from a sample group of organism, sorting as time series data and displaying and maintaining the luminescence measurement result group in real-time, receiving in real time another luminescence measurement result group from the sample group of organism, and displaying and maintaining the another luminescence measurement result group in real-time, instead of the luminescence measurement result group.

In the present invention, measurement data under bioluminescence measurement can be recognized in real-time by an operator, so that the measurement condition and the like can be controlled flexibly. For example, the measurement period of time can be shortened on the measurement data and another measurement preparation can be realized thereon. Therefore, the measurement efficiency in bioluminescence measurement can be raised.

In a preferred embodiment of the present invention, this invention is characterized by preparing a bioluminescence measurement result groups, receiving first luminescence measurement result groups in real-time from the sample groups with time stamp, sorting as time series data and displaying and maintaining the first luminescence measurement result groups in real-time, receiving second luminescence measurement result groups in real-time from the sample groups with time stamp, sorting as time series data and displaying and maintaining all luminescence measurement result groups in real-time, and repeating these sequences automatically.

In this case, if a plate with 96 wells is used, data of 96 samples can be treated simultaneously. Therefore, a large amount of data in the bioluminescence measurement can be recognized in a short period of time by an operator. With the combination of a given printing means with the above-mentioned preferred embodiment, the large amount of data can be printed by various scales to be recognized visually in a short period of time.

In another preferred embodiment of the present invention, the luminescence measurement result group and the others another luminescence measurement result group are stored and compared through reading out. Moreover, the luminescence measurement result groups and the others are stored and compared through reading out.

In this case, since the large amount of data in the bioluminescence measurement can be stored in real-time, the data can be compared with each other in real-time. Therefore, the bioluminescence with time can be recognized in real-time. In this point of view, the bioluminescence measurement can be performed as follows:

(A) The culture condition can be varied appropriately on the feedback of the measurement data.

(B) Response for external stimuli given to samples is recognized in real-time as changes of bioluminescence levels.

(C) The measurement is performed in a minimum period of time to be required.

In mutant screening, since the appropriate measurement condition is determined at every measurement, the function (A) is important. In mutant screening, the function (C) is also important because as much as possible samples must be measured in a short period of time. In the analyzing of isolated mutants, the function (B) is much important because this function enables us to analyze the response of reporter gene expression in the mutants to stimuli in detail and in real-time.

In still another preferred embodiment of the present invention, the rhythm of at least one of the luminescence measurement result group and the another luminescence measurement result group is analyzed. Moreover, the rhythm of at least one of the first luminescence measurement result groups and the second luminescence measurement result groups are analyzed.

In the measurement and analysis using a plate (e.g., with 96 wells) which contains sample in each well, conventionally, since data per plate are output as text files successively, each luminescence from each well of the plate can be recognized. In the above-mentioned preferred embodiment, each luminescence corresponding to each well of the plate can be measured with time, and plotted in the plot drawing area of the analyzing program in the present invention.

In general, luminescence from each well of the plate is changed with time as follows:

(A) Linear regulation: each luminescence is increased or decreased with time
(B) Periodic regulation: each luminescence is increased and decreased periodically, which is effective in the calculation of luminescence period, phase at minimum luminescence and maximum luminescence, amplitude of luminescence oscillation, or precision of the calculated luminescence period.

In a further preferred embodiment of the present invention, mutant screening is performed statistically.

In this case, since the mutant screening is carried out on the statistical processing function, the average, standard deviation and variance of the measurement results can be easily obtained and we can use these data to judge and select mutants. Therefore, a large-scaled mutant screening can be carried out easily and rapidly on the statistical processing function.

In a still further preferred embodiment of the present invention, analysis data on the luminescence measurement result groups group and the another luminescence measurement result group are output. Moreover, analysis data on the first luminescence measurement result groups and the second luminescence measurement result groups are output.

In this case, the average, standard deviation and variance of the measurement results can be easily recognized. For example, if 20 plates are used, the average, standard deviation and histogram of maximum 1920 measurement results relating to period length and phase of rhythms can be easily calculated and displayed. The 1920 measurement results are obtained from 20 plates×96 wells. The histogram, for example, is illustrated by the abscissa axis relating to measurement data and the ordinate axis relating to data number.

In this case, the measurement analysis can be easily enhanced on the displaying function relating to the histogram and the like. All of the measurement results can be recognized simultaneously from the histogram displaying or printing, etc., to be investigated in a short period of time.

Conventionally, all of the measurement results can not be displayed and printed simultaneously because of the poor function. For example, the measurements results are displayed and printed at eight per paper (1920 measurement results are printed out at 240 papers). In this preferred embodiment, in contrast, the 96 measurement results can be recognized in only one display and 1920 measurement results can be printed at minimum 40 papers.

With the above-mentioned preferred embodiments, the bioluminescence real-time measurement of the present invention becomes effective in the comprehensive genome function analysis and the comprehensive screening of mutant of post-genome.

Recently, genome sequences of various organisms have been determined, and comprehensive analysis for genome function is carried out on the genome sequences. The comprehensive analysis is usually carried out by the DNA array method. The function of the DNA array method can be complemented by the present invention, and the present invention is useful in the research of gene expression in real-time and large-scale. Therefore, the present invention is key point in the comprehensive analysis of genome function.

According to the present invention, the measurement data can be analyzed precisely and easily, compared with a conventional technique as mentioned above. In the conventional technique, the measurement data are analyzed on MS-DOS program driven through Excel macro program, which inhibits the drive of another program during the analysis. In addition, some measurement data not required in analysis can not be removed. In the present invention, in contrast, analysis condition such as analysis period and analysis parameters can be controlled on the measurement results due to the real-time measurement and analysis.

Other features and advantages of the present invention will be described in detail hereinafter.

BRIEF DESCRIPTION OF THE DRAWINGS

For better understanding of the present invention, reference is made to the attached drawings, wherein.

DESCRIPTION OF THE PREFERRED EMBODIMENTS

This invention will be described in detail with reference to the accompanying drawings, but is not limited to the following embodiments.

(1) Sample of Organisms

Figure 1A:
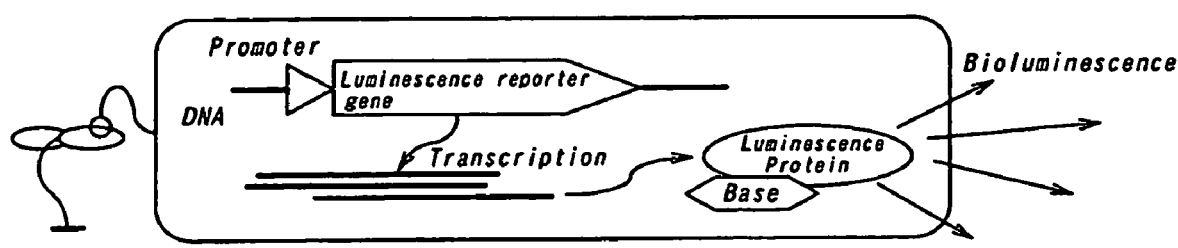
FIG. 1A is a schematic representation of the bioluminescent reporter system.
Figure 1B:
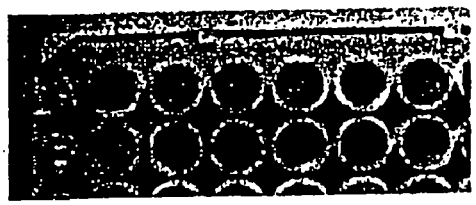
FIG. 1B is a photograph showing a portion of a measurement sample where the organism containing bioluminescent reporter gene are prepared in 96 wells of a plate.

In the present invention, since bioluminescence is measured, a sample of organisms should contain bioluminescence reporter gene. The sample of organisms is made by genetic engineering. In the genome of the organisms, a bioluminescent reporter gene, such as firefly luciferase gene and bacterial luciferase gene, is fused to the promoter region of the target gene which controls the gene expression, so that the transcriptional activities of the target gene in the living cell can be monitored as bioluminescence in real-time (FIG. 1A). Cells of organism which contains bioluminescent reporter gene is placed into each 96 well of a plate and the plate is sealed by a plate seal (FIG. 1B).

In the present invention, the rhythm analysis function and the display-print function are applied to all kinds of measurement data, such as Excel files and text files, by the reading function of the program in present invention. For example, more than 3000 gene expression measurement data, obtained by DNA array, can be analyzed on the program in present invention.

In the present invention, the real-time bioluminescence measurement can be applied to all organisms. The analyzing program in the present invention can be applied to analyze various biological phenomena as follows:

Analyzing electric signals generated from cultured neuron cells, analyzing oscillation of mitotic rate of cultured cell, analyzing oscillation of hormone concentration, neuron pulse at the insertion into a brain in animal, analyzing activity of an organisms from bacteria to fly to human beings, analyzing oscillation of body temperature and blood pressure in animal, and analyzing rhythms of leaf movement in higher plant.

(2) Bioluminescence Measurement Apparatus

Figure 2:
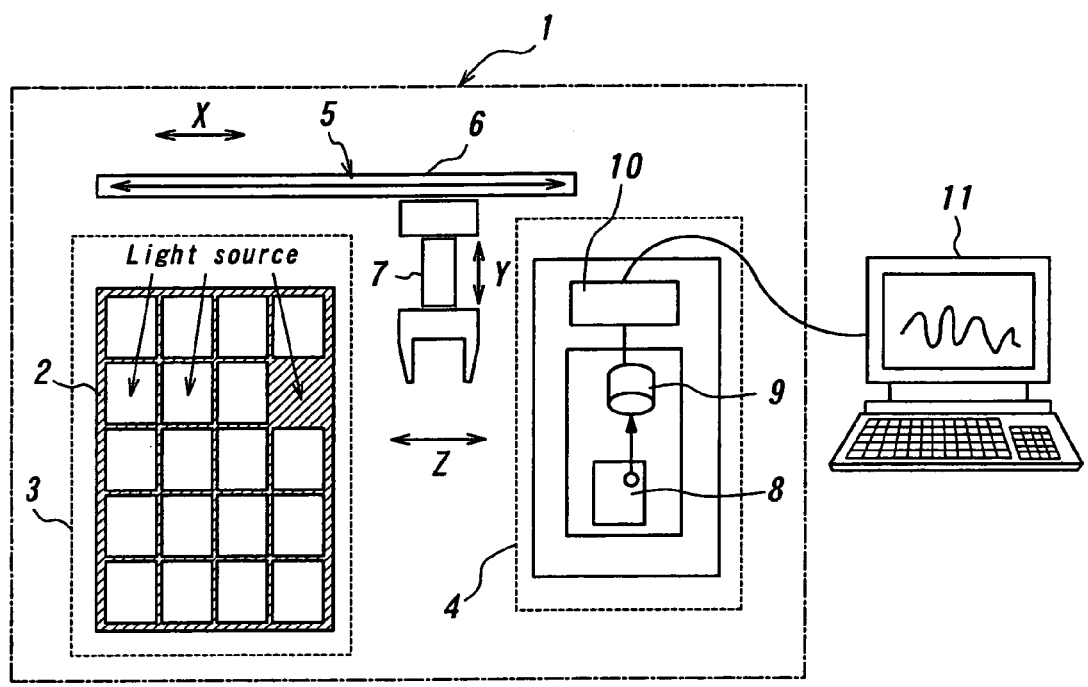
FIG. 2 is an explanatory view of apparatus for measurement of bioluminescenc according to the present invention.

As shown in FIG. 2, the bioluminescence measurement apparatus 1 includes the cultivating unit 3 where the organisms 2 (prepared into 96 wells of the plate) is set, the luminescence measurement unit 4, and the conveying unit 5 which conveys the samples 2 to the measurement unit 4 from the cultivating unit 3 or to the cultivating unit 3 from the measurement unit 4.

In the cultivating unit 3, the samples 2 are cultured under uniform condition. The conveying unit 5 is composed of the conveying rail 6 laid between the cultivating unit 3 and the bioluminescence measurement unit 4 and the conveying arm 7 to be moved between the cultivating unit 3 and the measurement unit 4. The conveying arm 7 is movable along the directions X, Y, Z. The culture condition on the cultivating unit 3 and the conveying condition of the conveying unit 5 awe controlled on the built-in sequential controller (not shown). The plate number, the measurement cycle and the measurement timing are controlled by the built-in sequential controller. The operations of the cultivating unit 3 and the conveying unit 5 can be carried out with the equipped touch panel electrically connected to the sequential controller. The samples 2 are measured at the bioluminescence measurement unit 4 which is a scintillation counter controlled by sequential controller via RS232C.

(3) Bioluminescence Measurement Unit

The bioluminescence measurement unit 4 includes the sample setting unit 8, the photon detector 9 which consists photomultiplier tubes to measure luminescence from the samples 2, and the built-in computer 10 to receive signals from the photon detector 9. The bioluminescence measurement is carried out on the control signal from the built-in computer 10 after the samples 2 are set in the measurement unit 4. The measurement is carried out successively at each well of the plate, and them, at every plate. The obtained measurement results are transferred to the external computer 11, and stored into a designated directory thereof. Real-time bioluminescence monitoring and analyzing software in the external computer 11 read the transferred results from the directory and analyze the data in real-time.

If the real time bioluminescence monitoring is carried out on the computer to control the hardware, different from the present invention, there will be some problems as follows:

(A) The bioluminescence measurement is disturbed due to the error by an operator.

(B) The culture conditions of organisms on the cultivating unit 4 is affected and fluctuated when an operator goes in and out the room set on the measurement apparatus and cultivating unit 4.

(4) Analyzing the Bioluminescence Data

① Real-Time

In the present invention, the measurement results of bioluminescence are received and analyzed in real-time at the external computer 11. If it takes six minutes in bioluminescence measurement per one plate (total 20 plates) and the measurement results per plate are transferred to the external computer 11, it takes 120 minutes in the total bioluminescence measurement of 20 plates. In one cycle of measurement, therefore, the total measurement results of 20 plates are transferred into the external computer 11 at every 120 minutes. In the present invention, the "real-time" means the cyclic time duration.

In the general bioluminescence measurement, since it takes one through seven days to complete the measurement, the cyclic time duration is short enough to realize the real-time measurement. The measurement can proceed at every several hours, which is very short in comparison with the total measurement period of time.

② The measurement results can be displayed and stored in real-time commensurate with the real-time measurement as mentioned above. In this case, the three functions are important as described in paragraph [0012].

③ The real-time measurement traces the luminescence with time at each data point, that is, each well of the plate with the corresponding sample therein. In the case of measuring and analyzing biological rhythms, since the luminescence is periodically changed with a period length about 24 hours, the rhythm analysis can be carried out for the measurement results by the program described in this invention.

The rhythm analysis is carried out by means of a conventional technique such as cosinor method or visual inspection method with linear regression (see, [Research of living body rhythm by Ken-ichi Honma et al., published by Hokkaido University, etc.]. With the cosinor method, various cosine waves with their respective periods are generated, and one cosine wave most resembling to the measurement results is selected from among the cosine waves. Therefore, the periodicity of the measurement results can be determined. With the visual inspection method, the peaks of the measurement results is detected, and the periodicity of the measurement results is determined on the time duration between the adjacent peaks in period of time.

④ Statistical Analysis

The statistical analysis of the present invention will be described in detail. As mentioned above, the average, standard deviation and histogram of the measurement results (e.g., 1920 measurement results) relating to period length and phase of rhythms can be easily calculated and displayed. The histogram is illustrated by the abscissa axis relating to measurement data and the ordinate axis relating to data number. In this case, the standard data distribution can be recognized from the histogram and a mutant can be easily recognized by the deviation from the standard data distribution.

The sample of organisms relating to the deviation from the standard data distribution is selected on "Pickup Window". If the selecting period length is set to 28 hours or over and the luminescence intensity is set to 20 thousands or over for the measurement results with a period range of 24 hours and a luminescence intensity range of 10 thousands, a longer in period and stronger in intensity can be selected (e.g., depicted as dot on the window).

Figure 6:
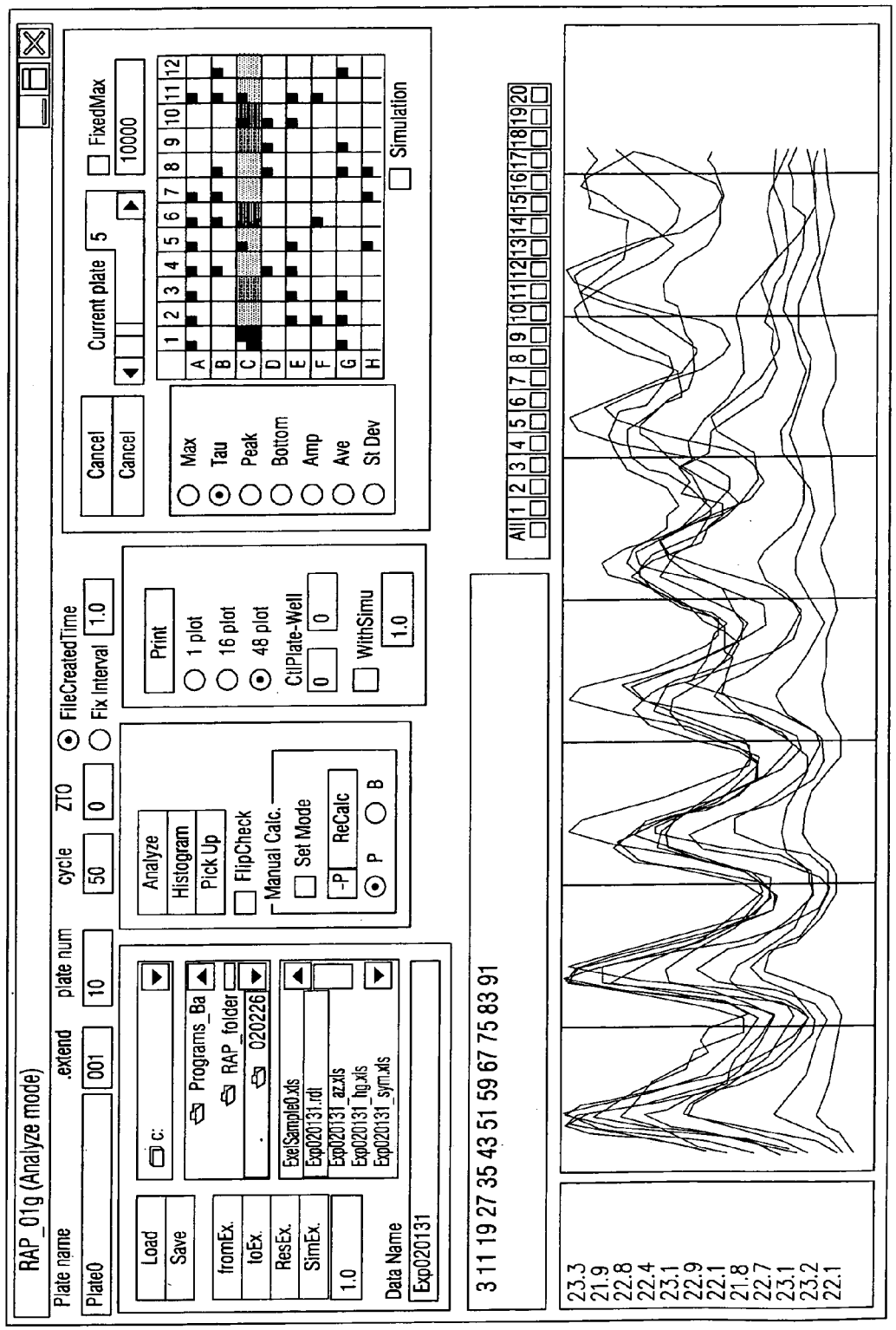
FIG. 6 shows an enlarged window relating to FIG. 3C.
Figure 7:
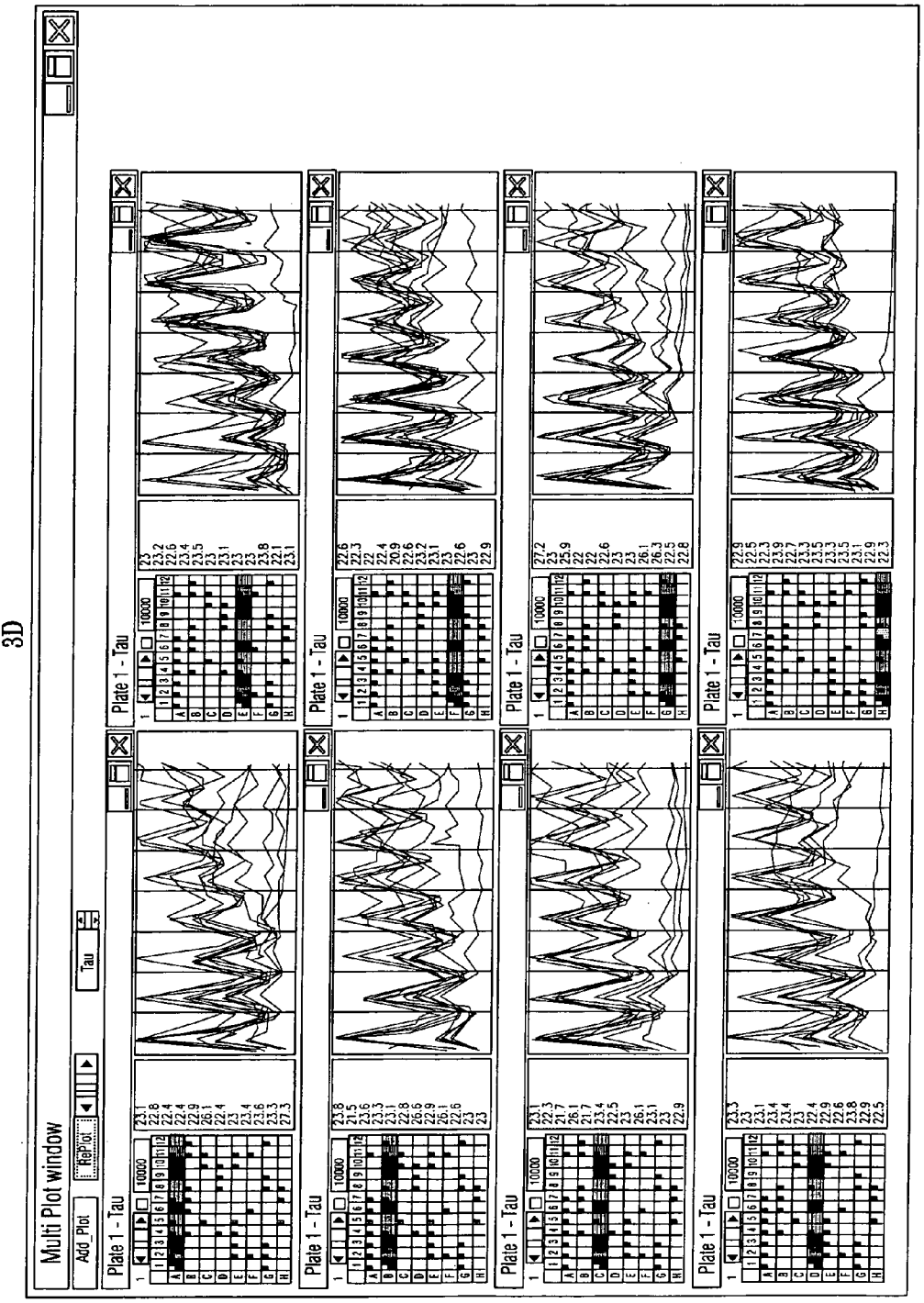
FIG. 7 shows an enlarged window relating to FIG. 3D.

The analysis process will be described with reference to FIG. 3. The display illustrated in FIG. 3 belongs to the external computer 11 illustrated in FIG. 2 or another computer. FIG. 4 shows some enlarged windows relating to FIGS. 3A, 3E, 3F and 3G, and FIG. 5 shows an enlarged window relating to FIG. 3B. FIG. 6 shows an enlarged window relating to FIG. 3C, and FIG. 7 shows an enlarged window relating to FIG. 3D.

(1) FIG. 3A

FIG. 3A relates to a software driving window of the computer to determine measurement or analysis.

(2) FIG. 3B

FIG. 3B relates to a software window under measurement of the computer which is switched in displaying. The measurement data relating to the selected button of the plate arranged upper right in the display is displayed in the drawing area arranged below in the display.

(3) FIG. 3C

FIG. 3C shows an analysis window of the computer which is switched in displaying. The windows relating to FIGS. 3E–3G are accessed from the analysis window. The analyzed results are displayed and printed from the analysis window, and output to another spreadsheet software from the analysis window.

(4) FIG. 3D

FIG. 3D shows a mass displaying window of the computer for 96 samples which is switched in displaying. The mass displaying window is accessed from the window relating to FIG. 3D or FIG. 3C.

(5) FIG. 3E

FIG. 3E shows an analysis condition window of the computer which is switched in displaying. In this window, the calculation condition and/or the analysis condition are determined. In this window, for example, the measurement results are analyzed in the following calculation:

① Calculation A

Peak recognizing method: The peaks of the rhythms are recognized by means of visual inspection method and analyzed.

Bottom recognizing method; The troughs of the rhythms are recognized by means of visual inspection method and analyzed.

According to the above-mentioned analysis, the peaks and troughs of the rhythms can be recognized automatically. If some peak or trough positions automatically recognized by the program are incorrect, these positions can be corrected manually and the rhythm analysis can be performed precisely through the recalculation.

(Calculation Condition)

Analysis data range: The data range of the measurement results to be analyzed is determined. The normal data range is set to the entire range of the measurement results.

Smoothing ON/OFF: The normal smoothing condition is set to "ON". In this condition, it is selected whether the original measurement results are analyzed or the smoothed measurement results through moving average are analyzed.

Calculation period range: The normal calculation period range is set to "ON". If the distance between the adjacent peaks or the adjacent troughs of the rhythms is beyond a predetermined range, additional peaks or bottoms are automatically added to or deleted from the measurement results through compensation.

② Calculation B

Cosinor method: The most proximate cosine wave is calculated by means of cosinor method. The cosinor method is suitable for the calculation of rhythms with much noise or with long distance of peaks or troughs. The cosinor method enables the rhythms of the measurement results to be calculated.

(Calculation Condition)

Analysis data range: The data range of the measurement results to be analyzed is determined. The normal data range is set to the entire range of the measurement results.

Simple calculation ON/OFF: The simple calculation condition is set to "ON". In this condition, the multiple rhythms of the measurement results are not analyzed, and the calculation period range is set within a given range. As a result, the speed of calculation is enhanced.

Calculation period range: The normal calculation range of period length is set to "ON". The period length of the cosine wave to be approximately calculated by means of cosinor method is defined within the calculation period range.

(5) FIG. 3F

FIG. 3F shows a statistical analysis window of the program on the computer which is switched in displaying. The measurement results of all of the plates where the samples of organisms are prepared are statistically analyzed, displayed and printed through the program described here.

(6) FIG. 3G

Figure 3:
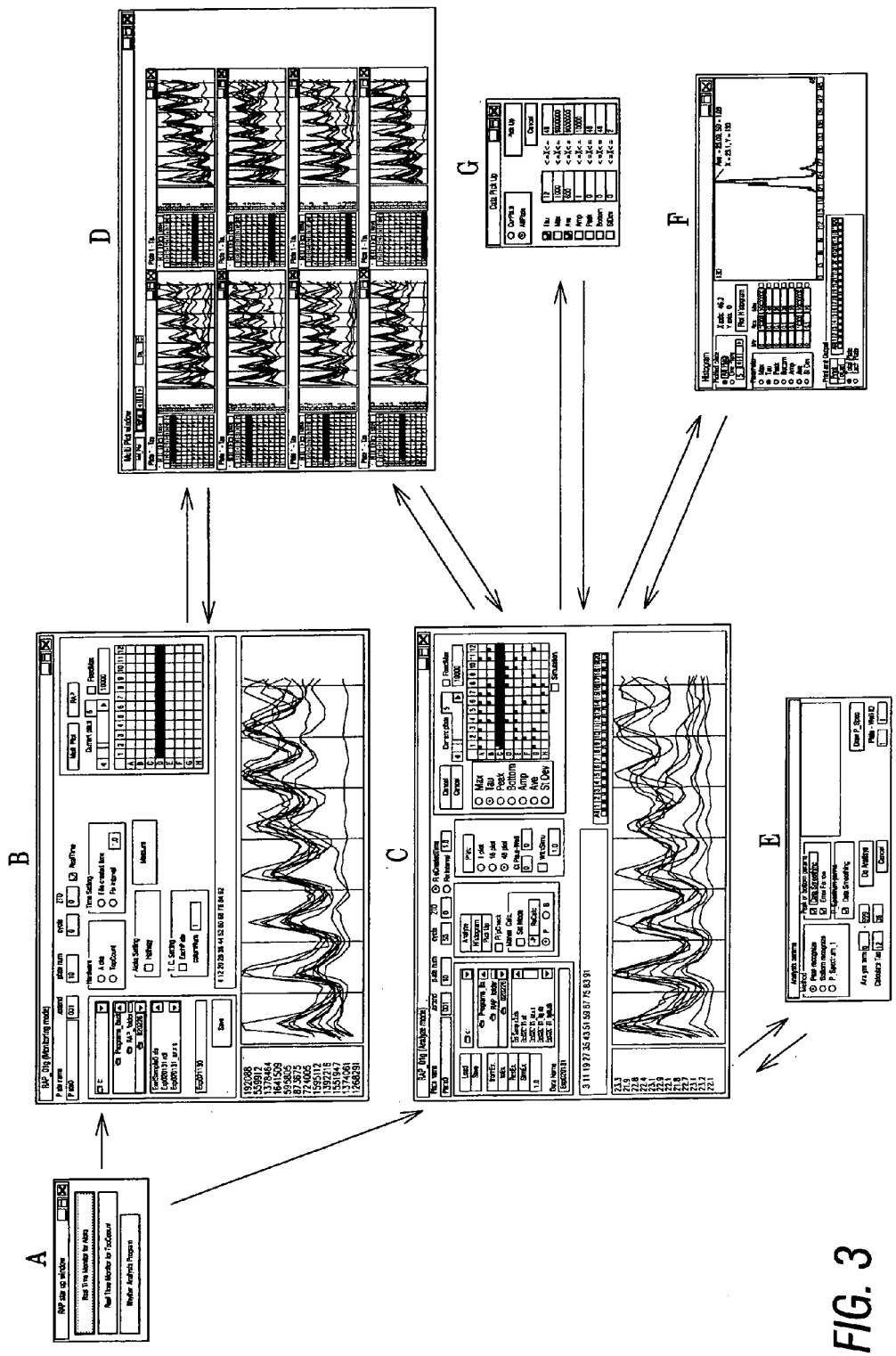
FIG. 3A shows a software driving window of a computer to be employed in the measurement.
FIG. 3B shows a software window under measurement of the computer which is switched in displaying.
FIG. 3C shows an analysis window of the computer which is switched in displaying.
FIG. 3D shows a mass displaying window of the computer for 96 samples which is switched in displaying.
FIG. 3E shows an analysis condition window of the computer which is switched in displaying.
FIG. 3F shows a statistical processing window of the computer which is switched in displaying.
FIG. 3G shows a pickup window of the computer which is switched in displaying.
Figure 4:
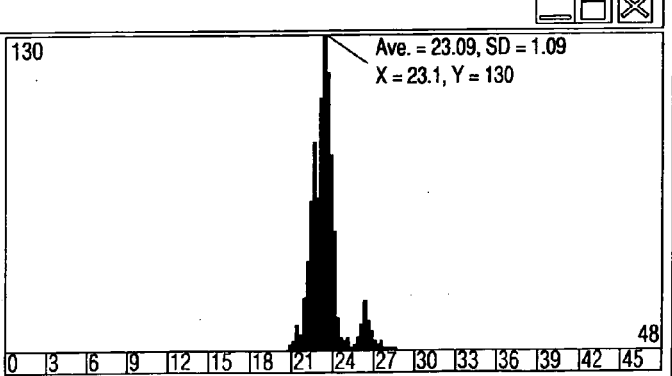
FIG. 4 shows some enlarged windows relating to FIGS. 3A, 3E, 3F and 3G.
Figure 5:
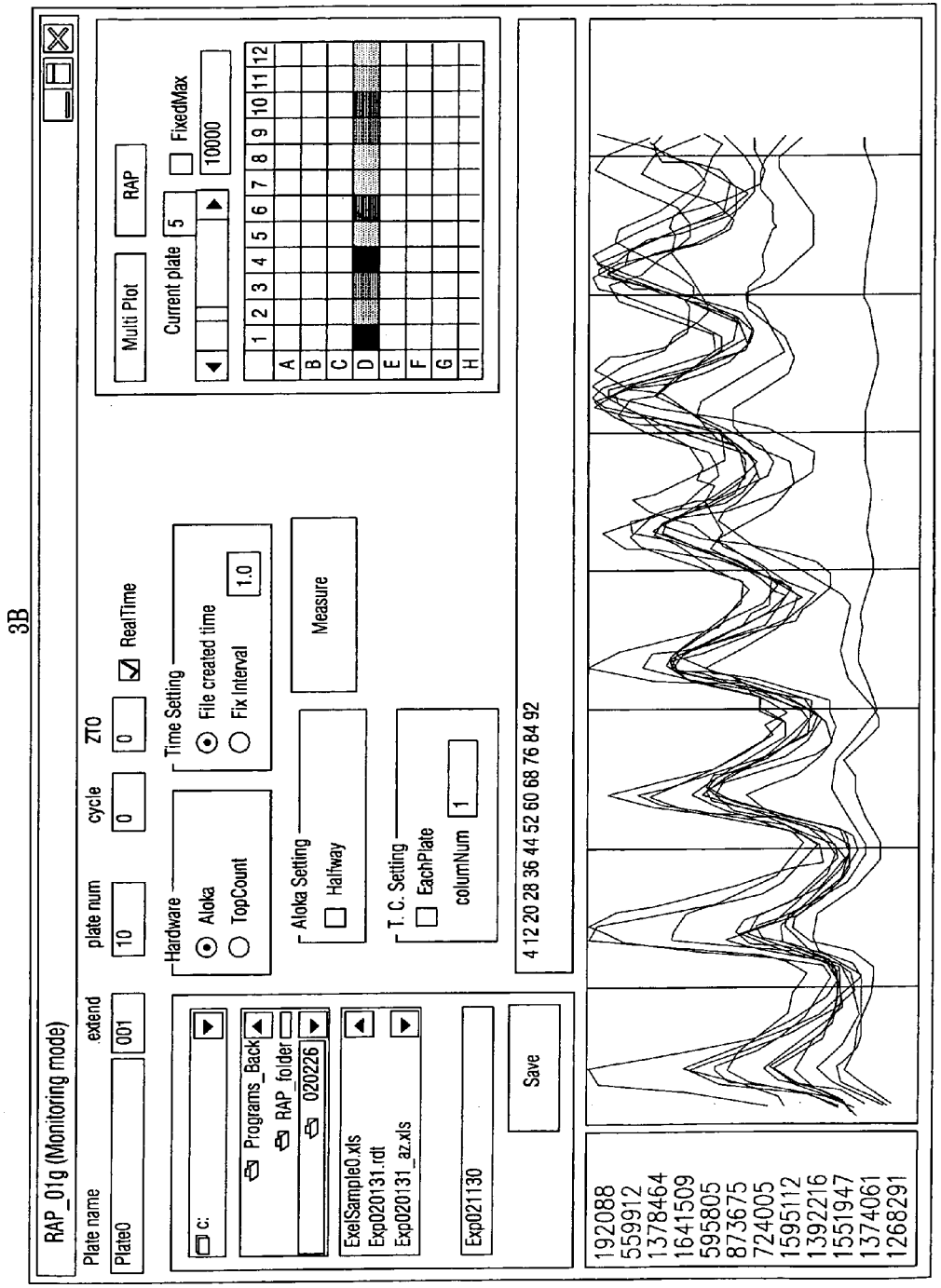
FIG. 5 shows an enlarged window relating to FIG. 3B.

FIG. 3G shows a pickup window of the program on the computer which is switched in displaying. In this window, the selecting condition to pickup some measurement results beyond the normal distribution is determined. The pickup measurement results are represented by dots on the well selecting area provided upper right in FIG. 3(*c*). This pickup window is used in order to select samples such as screened mutant that are defined by whether the measurement result relating to the mutant is beyond the upper limit and the lower limit.

EXAMPLE

A plurality of plates, each with 96 wells, are prepared on the cultivating platform installed in the bioluminescence measuring apparatus, and measured per plate under cultivation. In this case, the plates are successively conveyed into the measurement unit. The luminescence from the samples in the plates are measured with the photon detector, and the thus obtained measurement results are transferred to the external computer. The measurement results are analyzed and displayed in real-time by the program in the present invention. After the measurement and analysis, the plates are brought back onto the cultivating platform. The above-mentioned process is repeated per measurement and analysis of one plate (FIG. 2).

According to the present invention, the measurement results can be displayed in real-time under measurement (FIG. 3B). On the real-time measurement, various measurement conditions can be flexibly set, and the measurement period of time can be shortened. Moreover, since measurement results relating to the same plate or the different plates can be displayed simultaneously, they can be compared simultaneously and simply (FIG. 3D). The analysis for the measurement results can be performed under measurement (FIG. 3C). In the mutant screening, a mutant can be selected statistically and easily at the exclusive window (FIGS. 3F and 3G).

What is claimed is:

1. An apparatus for measuring and analyzing bioluminescence, comprising:
   a receiving means to receive a luminescence measurement result group in real-time from a sample group of organisms,
   a measurement controlling means to output a control signal for receiving said luminescence measurement result group,
   a sorting means to sort said luminescence measurement result group, and
   a displaying and maintaining means to display and maintain in real-time said luminescence measurement result group.

2. The apparatus as defined in claim 1, further comprising a comparing means to compare data of said luminescence measurement result group.

3. The apparatus as defined in claim 1, further comprising a storing means to store said luminescence measurement result group.

4. The apparatus as defined in claim 1, further comprising an analyzing means to analyze the rhythm of said luminescence measurement result group.

5. The apparatus as defined in claim 1, further comprising a statistical mutant screening means.

6. The apparatus as defined in claim 1, further comprising an outputting means to output analysis data on said luminescence measurement result group.

7. A program for measuring and analyzing bioluminescence, comprising:
   a receiving means to receive a luminescence measurement result group in real-time from a sample group of organisms,
   a measurement controlling means to output a control signal for receiving said luminescence measurement result group,
   a sorting means to sort said luminescence measurement result group, and
   a displaying and maintaining means to display and maintain in real-time said luminescence measurement result group.

8. The program as defined in claim 7, further comprising a comparing means to compare data of said luminescence measurement result group.

9. The program as defined in claim 7, further comprising a storing means to store said luminescence measurement result group.

10. The program as defined in claim 7, further comprising an analyzing means to analyze the rhythm of said luminescence measurement result group.

11. The program as defined in claim 7, further comprising a statistical mutant screening means.

12. The program as defined in claim 7, further comprising an outputting means to output analysis data on said luminescence measurement result group.

* * * * *